US005876334A

United States Patent [19]
Levy

[11] Patent Number: 5,876,334
[45] Date of Patent: Mar. 2, 1999

[54] LIE DETECTOR SYSTEM USING REACTION TIME

[76] Inventor: George S. Levy, 3980 Del Mar Meadows, San Diego, Calif. 92130-2258

[21] Appl. No.: 827,341

[22] Filed: Mar. 26, 1997

[51] Int. Cl.⁶ ..................................................... A61B 5/00
[52] U.S. Cl. ............................................................. 600/300
[58] Field of Search .................................... 600/300, 544, 600/545, 510, 523

[56] References Cited

U.S. PATENT DOCUMENTS

| | | | |
|---|---|---|---|
| 5,137,027 | 8/1992 | Rosenfeld | 600/544 |
| 5,170,780 | 12/1992 | Rosenfeld | 128/731 |
| 5,363,858 | 11/1994 | Farwell | 128/731 |
| 5,406,956 | 4/1995 | Farwell | 600/544 |
| 5,467,777 | 11/1995 | Farwell . | |
| 5,564,433 | 10/1996 | Thornton | 600/544 |
| 5,640,966 | 6/1997 | Heden et al. | 600/544 X |

Primary Examiner—Francis J. Jaworski

[57] ABSTRACT

Lie detection system utilizing manual or verbal reaction time to carefully crafted questions used to discriminate between liars and truth-tellers. The invention comprises the hardware and software required to perform the response speed test as well as the questionnaire composition methodology. Discrimination between liars and truth-tellers is enhanced by asking questions requiring simple answers such as "Yes," or "No," and containing an element of surprise to force the liar to manufacture lies on the spur of the moment. His task is further complicated by adding logical inversion levels in his mind using "lying-on-command," negations and double negations. Response time variations between individuals and between questions are reduced by means of controlled questions and controlled subjects, random delays in question presentation, delays in the key word presentation and randomization of question order. Strategies for countering countermeasures of liars are based on statistical techniques, priming and assigning concurrent tasks. Advantages include: no need to wire the subject to a machine, objective assessment made by computer software with minimal input from an operator, and remote operation of the device through a telecommunication medium (modem).

31 Claims, 2 Drawing Sheets

LIE DETECTOR SYSTEM USING REACTION TIME

This invention relates to lie detectors and more particularly to polygraphs. It also relates to psychology and to the measurement of response speed for the purpose of lie detection.

BACKGROUND OF THE INVENTION

Current lie detection methods, based on the polygraph technique, rely upon the measurement of several physiological characteristics to discriminate whether a truth or a lie is expressed. These measurements include skin resistivity, blood pressure, heart rate and respiration rate.

The most commonly employed procedure in criminal investigation is the Control Question Technique (CQT) used for formulating questionnaires. In this procedure, three types of questions are included: relevant (e.g., Did you rob the bank on March 2?), irrelevant (e.g., Did you graduate from high school?) and control (e.g., Have you ever stolen anything?). The control questions are designed to elicit an emotional response in innocent subjects that exceeds the response to the relevant questions. Relevant questions are designed to elicit large emotional response in guilty subjects. The role of the examiner is to formulate the questions and to interpret the results. Another approach, the Guilty Knowledge Test (GKT) presents the subject with information known to him but unknown to the public. The subject is asked relevant questions and control questions. Relevant questions contain information about the crime designed to arouse the subject if he is guilty, and control questions are designed to arouse him if he is innocent. This procedure relies on the assumption that autonomic arousal is induced in the guilty subject by aspects of the transgressive act and situation known only to him.

These methods describe above require the availability of a polygraph machine and the presence of qualified personnel to wire up the subject, and administer and interpret the test.

Direct electro-encephalographic (EEG) measurements of event-related brain potentials (ERP) to particular questions or situations, can also be used. ERP components relevant to lie detection are the endogenous components representing brain processing that occur after the earliest, sensory driven, exogenous components die down. Researchers have used the amplitude of endogenous components, notably P300 and N400, in lie detection studies [Bashore 77]. Thus brain potential studies have demonstrated the existence of larger amplitude delayed responses in deception situations.

These techniques, still experimental, also require, like classical polygraphy, the availability of ERP machines and of competent personnel to wire test subjects and to interpret results.

State of the art lie detection methods rely on specialized equipment and highly trained personnel to administer tests. While advances in brain monitoring technology provides opportunities for more precise tests using expensive equipment such as EEG, there is a need for simple, easy to use, accessible and reliable devices that can be used locally or at a distance, without having to wire up the subject. Benefiting organizations would include the FBI, CIA, Armed Services, IRS, as well as drug testing programs, educational institutions and public sector businesses such as credit card companies and banks.

This invention is justified by the experimentally observed fact that endogenous components of brain activity can be delayed with increased brain processing [Bashore 93], and [Ritter, Simson and Vaughan] and [Kutas et al, 1977]. Significant delays in electro-encephalographic response time (RT) have also been observed in response to increased brain processing [Kutas et al, 1977]. Farwell et al [8], in particular, shows that event-related brain potentials can be used in interrogative polygraphy. In U.S. Pat. Nos. 5,467,777, 5,406,956 and 5,363,858 Farwell describes lie detection methods using electro-encephalography. In U.S. Pat. No. 5,170,780 Rosenfeld uses electro-encephalography to measure the P3 brain wave to perform lie detection.

It is an object of this invention to provide a simple yet effective lie detection system based on time measurements of voluntary physical motor responses, such as manual or vocal reaction times, and a judiciously chosen questionnaire composition methodology.

It is another object of the invention to provide a lie detection method that does not require having to wire up the test subject.

It is another object of this invention to provide a computerized and objective means of analyzing the data thus facilitating the task of the operator and providing for greater objectivity, uniformity, consistency and reliability of the test results, independently of the skill or interpretation of the operator.

It is yet another object of this invention to provide a lie detection tests that can be administered locally, or at a distance. For example the subject could be responding through a keyboard to written questions sent to him through a radio or telecommunication link. Remote operation could also be in audio form in which the subject hears a question on a telephone and must answer it orally using a simple response such as "yes" or "no".

It is yet another objective to provide a lie detection system which operates on simple and readily available equipment requiring only a computer equipped with a real time clock, a monitor, a manual data entry device such as a keyboard, a mouse or a joystick, and software to administer a questionnaire and measure reaction time.

It is another object of this invention to provide a lie detection method that can work independently of, or conjointly with, other lie detection techniques.

Further objectives and advantages of my invention will become apparent from a consideration of the drawings and the ensuing description.

SUMMARY OF THE INVENTION

This invention uses delays in voluntary physical motor actions such as manual or vocal responses to questions carefully designed to increase mental processing in liars but not in truth tellers. The questions are entered in a computer database by the lie detection examiner. At test time, the questions are presented to the subject who must respond as quickly as he can, by means of very simple manual or vocal data entries. Delays in response are taken as an indication of untruthfulness. Variations in response time from one individual to another, and from one question to another are accounted for by means of control questions and control subjects respectively. Improved discrimination between liars and truth tellers can be achieved by setting up testing conditions that result in:

1) Increase in signal which consist of differences in response time caused by different mental processes between liars and truth tellers. These conditions include surprise, lying-on-command, negatives and double negatives, and concurrent tasks that interfere with lying.

2) Reduction in noise caused by biological, neurological and psychological states of the test subject, which are independent of lying. This reduction in noise is achieved by means of control questions, control subjects, randomization of question display delays, delays of key words, randomization of question order to eliminate the effect of context.

3) Countering of countermeasures used by liars to deceive this technique. Countering techniques include too fast/too slow tests that can identify response profile of persons who have rehearsed, priming that uses context and guilty knowledge to manipulate the frame of mind of a guilty person, and the assignment of concurrent tasks that interfere with the subject's own mental tasks.

A database of responses is collected and used to estimate the truthfulness of the tested subject. Remote testing is possible through a computer data communication link.

DETAILED DESCRIPTION OF PREFERRED EMBODIMENTS

Operation

Figure 1:
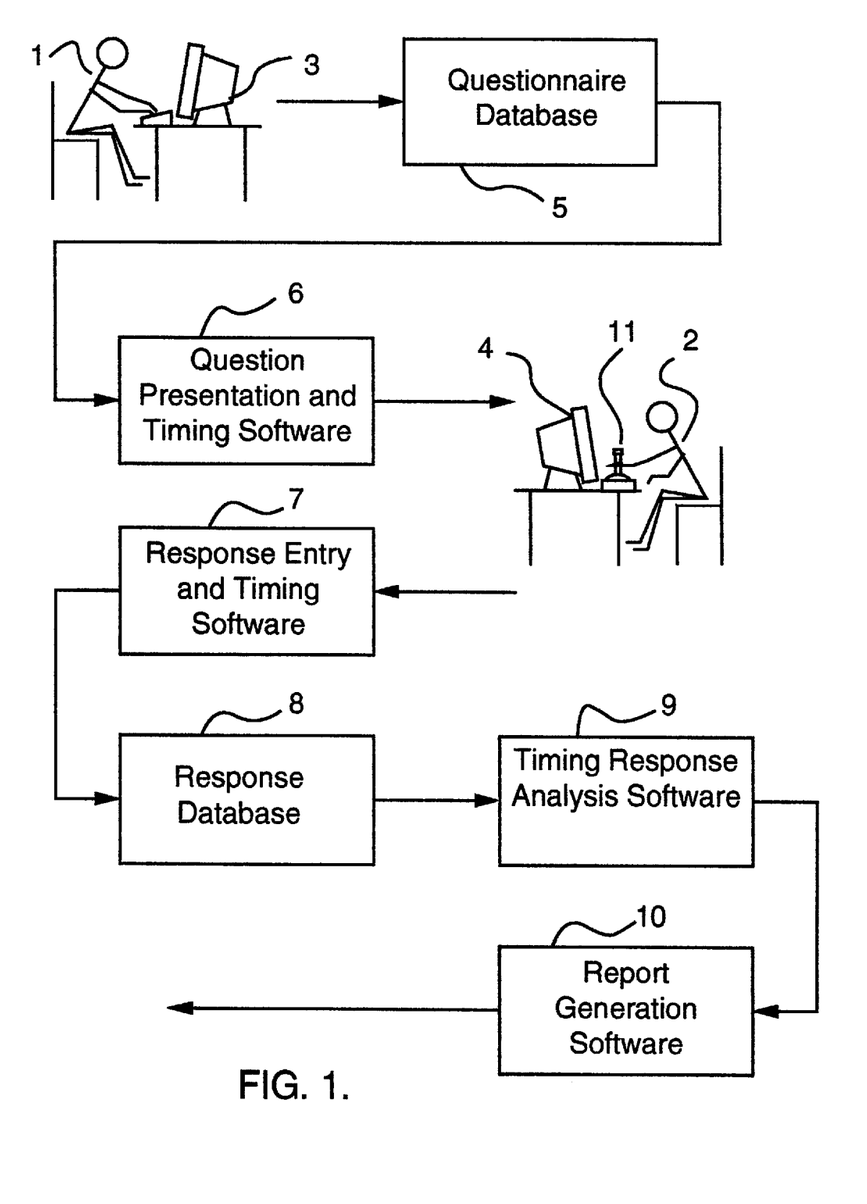
FIG. 1 illustrates the data flow including questionnaire composition, question presentation and timing software, response entry and timing software, response database, analysis software and report generation software.

As shown in FIG. 1, the lie detection examiner 1 composes on computer 3 a questionnaire which is entered into a questionnaire database 5. The Question Presentation and Timing Software 6, running on computer 4 displays the questions one at a time on a video monitor to a test or control subject 2. Alternatively the question could be presented to him in audio form by the computer.

The questions are of the multiple choice type and the test subject is required to answer these questions as quickly as possible. He enters his answer into the computer using a manual data entry device such as a joystick 11, a keyboard, or by depressing one of two buttons on a mouse. A simple implementation of the multiple choice is the binary choice ("Yes," "No") or even the simpler unary choice (Press a button if a condition, or a set of conditions is satisfied).

Alternatively the answer could be provided orally by the subject into a microphone and decoded by means of a voice recognition device by the computer.

His response time is defined as the time interval between the appearance of the question on the screen and his response through the data entry device.

The response data and timing are measured and recorded by the Response Entry and Timing software 7 which collects timing and data information entered by the subject and store it into the Timing Response Database 8.

This information is then used by the Timing Response Analysis Software 9 to estimate the truthfulness of the subject 2 and to classify him as a liar or as a truth teller. Estimation and classification are well known problems which can be solved using methods drawn from mathematical branches such as statistics or neural nets.

The Report Generation Software 10 generates a report outlining the lie detection test findings.

Theory

The approach outlined below aims at generating a questionnaire composition methodology and a reaction time processing technique to address the issue raised by the variability in the subject reading time, comprehension time and motor skills, and provide strategies to counter attempts by dishonest test subjects to foil the lie detection system.

The following topics are discussed:
1) Cognitive modeling
2) Modeling control questions and control subjects
3) Use of response data
4) Design of Question Set
5) Design of Question Presentation
6) Selection of concurrent tasks interfering with lying
7) Countering rehearsal
8) Filtering and Editing of Response Time Data
9) Entering question database
10) Remote operation
11) Integration with other lie detection techniques
12) Display of results

Cognitive modeling

A very simple cognitive model is adequate: when no lie is involved, the response time $T_{resp}$ to a question could be modelled as the sum of the reading and comprehension time plus the motor activation time. Let us call this sum $T_{true}$. Thus the response time can be expressed as:

$$T_{resp}=T_{true}$$

Questions can be designed such that if lying occurs, an additional time, $T_{lie}$, is needed to allow the lie to be manufactured in the mind of the liar. Thus, when lying is present, the response time $T_{resp}$ can be expressed as a sum:

$$T_{resp}=T_{true}+T_{lie}$$

Alternatively we can express $T_{resp}$ as a product:

$$T_{resp}=LT_{true}$$

where L=1 when the subject tells the truth and is typically greater than one when he lies.

Lie detection, then, depends on the ability to obtain an estimate for $T_{lie}$ or L.

A model can be developed that can help in separating out the increase in response time due to lying, from the time taken to parse and comprehend a question, and from the effect of the mental and physical state of the test subjects. Data for this model can be obtained from the following sources:

1) Irrelevant questions, control questions, guilty knowledge questions, and relevant questions
2) Innocent control subjects, and guilty control subjects
3) Test subject Irrelevant, control, guilty knowledge and relevant questions are well known in the field of polygraphy. Irrelevant questions have a neutral or non-threatening meaning as, for example, in "Did you graduate from high school"? Control questions are design to elicit an emotional response from most people as in "Have you ever stolen anything"? Guilty knowledge questions make use of information only known to the criminal, such as the location of the crime: "Have you ever been to this bank". Relevant questions are directly related to the critical incident: "Did you rob the bank?"

In this invention, irrelevant, control, and guilty knowledge questions are used to account for and possibly eliminate time differences in the response time of individuals, that are not caused by lying.

As shall be explained below several methods can be used to eliminate these time differences. One approach is to use questions designed to have approximately the same grammatical construction to reduce differences in reading, parsing and comprehension time as in the following examples:

Irrelevant Question:
Did you ever buy a tie from Mrs. Jackson?
(irrelevant questions are emotionally neutral)

Control question:
Did you ever tell a lie to your parents?
(Control questions are loaded with emotional keywords: "tell a lie", "steal a pie". They elicits an emotional response, typically from everybody.)

Guilty knowledge question (a pie has been stolen, but Mr. Anderson does not have pie):
Did you ever eat a pie at Mr. Anderson's?
(Guilty knowledge questions elicit an emotional response only in the guilty subject by using information only known to the criminal: Pies were stolen.)

Relevant question (Mrs. Johnson does have pies):
Did you ever steal a pie from Mrs Johnson?
(Relevant questions refer to the crime. They include an emotional component as well as a delay due to lying.)

Control subjects are data sources not classically used in polygraphy. There are two kinds of control subjects: innocent and guilty.

Innocent control subjects are innocent people who have no emotional attachment to any of the questions pertaining to the crime. These subjects provide a baseline against which the responses of guilty control subjects and of test subjects is measured.

Guilty control subjects are innocent people used to model some aspect of the liar's psyche. Several methods can be used to create such subjects. For example, in the context of a game or a skit, a control subject is assigned the task of committing a pretend crime mirroring the real crime under investigation. After the pretend crime, he is offered a reward if he fools a test for his pretend crime, identical to the one given to the suspected criminal for the real crime. Alternatively he can be threatened with a punishment, such as a mild electric shock, if he does not pass the test. Rewards and punishments have the purpose of bolstering the subject's emotional response to the questions.

Response time measurements $T_{resp}$ for questions and subjects can be organized in a matrix form:

|  | Innocent Control Subject | Guilty Control Subject | Test Subject |
| --- | --- | --- | --- |
| Irrelevant Question | $T_{IN}$ | $T_{IG}$ | $T_{IT}$ |
| Control Question | $T_{CN}$ | $T_{CG}$ | $T_{CT}$ |
| Guilty Knowledge Questions | $T_{KN}$ | $T_{KG}$ | $T_{KT}$ |
| Relevant Question | $T_{RN}$ | $T_{RG}$ | $T_{RT}$ |

The following index nomenclature is employed:
I=Irrelevant questions
C=Control questions
K=Guilty knowledge questions
R=Relevant questions
N=Innocent control subjects
G=Guilty control subjects
T=Test subjects One must keep in mind that in practice such a matrix is typically much larger because it may combine several questions and control subjects of each type. Conceivably, there could even be several test subjects if, for example, a criminal group sharing the same guilty knowledge is tested.

To combine together information from control questions, control subjects, and test subjects, one can express each element of above matrix as the product of four quantities:

$$T_{resp}=LEQS$$

where:
L is a factor standing for the increase in response time due to lying. It is equal to one if the subject tells the truth and is typically greater than one when the subject lies.

E stands for the time delay factor caused by the emotional content of the question.

Q models the time required to parse and comprehend a question.

S represents the time variations caused by the mental and physical state of the subject being tested.

While the mechanism for this delay involves complex brain processes, the simplicity of these models is justified since only the delay itself is of importance, not the underlying brain mechanism. The above equation is just one particular model example. Clearly for those knowledgeable in this field there are many alternative ways of expressing $T_{resp}$. For example, the model could be expressed as a polynomial or some other functional series expansion of the L, E, Q, S terms.

Thus the response time measurement matrix can be expressed in term of the model as:

|  | Innocent Control Subject | Guilty Control Subject | Test Subject |
| --- | --- | --- | --- |
| Irrelevant Question | $Q_I S_N$ | $Q_I S_G$ | $Q_I S_T$ |
| Control Question | $EQ_C S_N$ | $EQ_C S_G$ | $EQ_C S_T$ |
| Guilty Knowledge Question | $Q_K S_N$ | $EQ_K S_G$ | $EQ_K S_T$ |
| Relevant Question | $Q_R S_N$ | $L_G EQ_R S_G$ | $L_T EQ_R S_T$ | where:
$Q_I$=time required to parse and comprehend one irrelevant question $Q_C$=time required to parse and comprehend one control question $Q_K$=time needed to parse and understand a guilty knowledge question $Q_R$=time required to parse and comprehend a relevant question $S_N$=time required by an innocent control subject
$S_G$=time required by an guilty control subject
$S_T$=time required by an guilty control subject
$L_G$=time delay of the guilty control subject
$L_T$=time delay of the test subject Lie detection can be performed by estimating $L_T$. If the test subject is honest, $L_T$ equals 1. Otherwise, $L_T=L_G$. There are several ways to solve for $L_T$. A simple method is to take ratios of time measurements such as shown below.

$$\frac{L_T}{L_G} = \frac{T_{RT}T_{KG}}{T_{KT}T_{RG}}$$

Using the model yields:

$$\frac{L_T}{L_G} = \frac{L_T E Q_R S_T}{E Q_K S_T} \cdot \frac{E Q_K S_G}{L_G E Q_R S_G}$$

and $L_G$ can be estimated with $$L_G = \frac{(L_G E Q_R S_G)(Q_K S_N)}{(E Q_K S_G)(Q_R S_N)} = \frac{T_{RG}T_{KN}}{T_{KG}T_{RN}}$$

substituting into the expression for $L_T/L_G$ we can solve for $L_T$ in terms of time measurements:

$$L_T = \frac{T_{RT}T_{KG}T_{KG}T_{RN}}{T_{KT}T_{RG}T_{RG}T_{KN}}$$

The T's in the above expression represent measurements which can be used to estimate $L_T$.

A more powerful and general method of estimating $L_T$ involves using least square or a similar estimation technique. One could begin by taking the logarithms of all the model states and forming a vector:

$$x = q_I, q_C, q_K, q_R, s_N, s_G, s_T, e, I_G, I_T)$$

where:

$q_I = \log(Q_I)$
$q_C = \log(Q_C)$
$q_K = \log(Q_K)$
$q_R = \log(Q_R)$
$s_N = \log(S_N)$
$s_G = \log(S_G)$
$s_T = \log(S_T)$
$e = \log(E)$
$I_G = \log(L_G)$
$I_T = \log(L_T)$ The response time measurements can also be expressed as a vector, y, of logarithms:

$$y = (t_{IN}, t_{IG}, t_{IT}, t_{CN}, t_{CG}, t_{CT}, t_{KN}, t_{KG}, t_{KT}, t_{RN}, t_{RG}, t_{RT})$$

where:

$t_{IN} = \log(T_{IN})$
$t_{IG} = \log(T_{IG})$
$t_{IT} = \log(T_{IT})$
$t_{CN} = \log(T_{CN})$
$t_{CG} = \log(T_{CG})$
$t_{CT} = \log(T_{CT})$
$t_{KN} = \log(T_{KN})$
$t_{KG} = \log(T_{KG})$
$t_{KT} = \log(T_{KT})$
$t_{RN} = \log(T_{RN})$
$t_{RG} = \log(T_{RG})$
$t_{RT} = \log(T_{RT})$ Since a product such as $T_{IN} = Q_I S_N$ can be expressed as a sum of logarithms:

$$t_{IN} = q_I + s_N$$

we can represent the relationship between the state vector x and the measurement vector y by a matrix equation:

$$y = Hx$$

where H is a matrix of ones and zeros. For example the expression $$T_{RT} = L_T E Q_R S_T$$

can be expressed as:

$$t_{RT} = (0\ 0\ 0\ 1\ 0\ 0\ 1\ 1\ 0\ 1)x$$

A set of measurements may include several questions and subjects of each type. There may be j irrelevant questions, k control questions, m guilty knowledge questions, and n relevant questions. Similarly there may be p innocent control subjects, and q guilty control subjects. In case of group testing, if a criminal gang is suspected for example, there may even be r test subjects. For the sake of providing a simple illustration, we shall assume the simple case of one question and one subject of each type. The following example is unrealistic but is adequate for illustrating the concept. The matrix equation relating the measurement vector y to the state vector x is:

$$\begin{pmatrix} t_{IN} \\ t_{IG} \\ t_{IT} \\ t_{CN} \\ t_{CG} \\ t_{CT} \\ t_{KN} \\ t_{KG} \\ t_{KT} \\ t_{RN} \\ t_{RG} \\ t_{RT} \end{pmatrix} = \begin{pmatrix} 1 & 0 & 0 & 0 & 1 & 0 & 0 & 0 & 0 & 0 \\ 1 & 0 & 0 & 0 & 0 & 1 & 0 & 0 & 0 & 0 \\ 1 & 0 & 0 & 0 & 0 & 0 & 1 & 0 & 0 & 0 \\ 0 & 1 & 0 & 0 & 1 & 0 & 0 & 1 & 0 & 0 \\ 0 & 1 & 0 & 0 & 0 & 1 & 0 & 1 & 0 & 0 \\ 0 & 1 & 0 & 0 & 0 & 0 & 1 & 1 & 0 & 0 \\ 0 & 0 & 1 & 0 & 1 & 0 & 0 & 0 & 0 & 0 \\ 0 & 0 & 1 & 0 & 0 & 1 & 0 & 1 & 0 & 0 \\ 0 & 0 & 1 & 0 & 0 & 0 & 1 & 1 & 0 & 0 \\ 0 & 0 & 0 & 1 & 1 & 0 & 0 & 0 & 0 & 0 \\ 0 & 0 & 0 & 1 & 0 & 1 & 0 & 1 & 1 & 0 \\ 0 & 0 & 0 & 1 & 0 & 0 & 1 & 1 & 0 & 1 \end{pmatrix} \begin{pmatrix} q_I \\ q_C \\ q_K \\ q_R \\ s_N \\ s_G \\ s_T \\ e \\ I_G \\ I_T \end{pmatrix}$$

When the number of questions per type is greater than one, as is generally the case, the measurement and state vector are increased accordingly. Thus, in general, the state vector would have j elements corresponding to irrelevant questions, plus k elements corresponding to control questions and so on. The elements e representing emotional response can, in general, remain single unless several "levels" of emotional arousal need to be modeled. Similarly the element IG corresponding to the lying delay of guilty control subjects can also remain single unless several "capabilities" for lying of the control subjects needs to be modeled. The measurement vector y increases in dimension in proportion to the number of measurements taken.

The state vector x can be solved using the least square method.

$$x = (H^T H)^{-1} H^T y$$

where $H^T$ is the transpose of H. The last element $I_T$ of x can be used to compute $L_T$:

$$L_T = \text{antilog}(I_T)$$

Other techniques borrowed from estimation theory and statistics, are available to solve this problem, including Weighted Least Square, Kalman Filtering, and Neural Nets. For example, the Weighted Least Square formulation is $$x = (H^T W H)^{-1} W H^T y$$

where W is a symmetrical weighting matrix to be optimized.

Kalman filtering and derived techniques solve this optimization problem and can estimate measurement noise as well as state noise. When the measurements are applied one at a time in the estimation process, the measurement vector is a scalar. In this case, the Kalman filter formulation takes a recursive form and can be represented as:

$$\underline{x}_{k+1} = \frac{PH^T}{HPH^T + R} (\underline{y} - H\underline{x}_k)$$

where k is the recursive index, P is the state covariance matrix and R is the measurement variance. The set of equations required to calculate the P matrix is well known in the field of estimation theory and can be referred to in "Least Square Estimation from Gauss to Kalman", IEEE Spectrum 7, 63–68 by Sorenson H. W. (1970). Efficient versions of the Kalman filter algorithms can be found in "Factorization Methods for Discrete Sequential Estimation" by Gerald Bierman.

Neural Nets offer an alternative method of computing W. A two layer net can be set up, with the first layer being the measurement vector y, and the output layer, the state vector x. The interconnection matrix can be chosen to be initially identical with $(H^TH)^{-1}H^T$. Backpropagation can then be used to refine the interconnection weights. An advantage of the neural net approach is that it can go beyond the estimation of $L_T$ and embodies a classification mechanism. A good discussion of neural net techniques is provided in *Artificial Neural Systems*, by Patrick K. Simpson, Pergamon Press, 1990.

This estimation problem can be solved in many other ways derived from statistics as is well known to professionals in this field.

Use of Response Data

Data collected during the interrogation process does not include just timing data. It also comprises response information such as "yes" or "no" answers to questions. This information can be used together with the timing data in the lie detection process. There are many ways of doing this. The simplest is to consider only the answer data produced by the test subject answering relevant questions. An admission of guilt to a questions such as: "did you fire the gun" with an answer "yes" renders moot the timing analysis.

A more complex approach involves using answer data to irrelevant, control, and guilty knowledge questions to derive an index of truthfulness for the test subject. For example, let us define a function "Truth" as follows:

Truth (answer to question is true)=1

Truth (answer to question is false)=−1

Truth (answer to question cannot be verified)=0

A vector d for the test subject can be defined as:

$$d = (d_{IN}, d_{IG}, d_{IT}, d_{CN}, d_{CG}, d_{CT}, d_{KN}, d_{KG}, d_{KT}, d_{RN}, d_{RG}, d_{RT})$$

where $d_{IN}$=Truth(answer to irrelevant question by innocent control subject)

$d_{IG}$=Truth(answer to irrelevant question by guilty control subject)

$d_{IT}$=Truth(answer to irrelevant question by test subject )

$d_{CN}$=Truth(answer to control question by innocent control subject)

$d_{CG}$=Truth(answer to control question by guilty control subject)

$d_{CT}$=Truth(answer to control question by test control subject)

$d_{KN}$=Truth(answer to guilty knowledge question by innocent control subject)

$d_{KG}$=Truth(answer to guilty knowledge question by guilty control subject)

$d_{KT}$=Truth(answer to guilty knowledge question by test control subject)

$d_{RN}$=Truth(answer to relevant question by innocent control subject)

$d_{RG}$=Truth(answer to relevant question by guilty control subject)

$d_{RT}$=Truth(answer to relevant question by test subject)

If the answer to a question such as an irrelevant or control question can be independently verified, then the truth function for the answer given by the test subject can easily be produced. The truth value for some of the answer are $d_{IT}$, $d_{CT}$, and $d_{KT}$. Wrong answers to those questions indicates a propensity of the test subject to be in a "lying frame of mind" and to want to deceive the test. A guilty answer on $d_{RT}$ obviously is an indication of guilt.

Thus a truthfulness index can be calculated by means of a sum or a weighted sum of $d_{IT}$, $d_{CT}$, and $d_{KT}$.

Neural nets offer a powerful method for fusing both timing and data information. The input nodes of a neural net can easily be extended to include both the y response timing vector, and the d answer data vector:

$$z(t_{IN}, t_{IG}, t_{IT}, t_{CN}, t_{CG}, t_{CT}, t_{KN}, t_{KG}, t_{KT}, t_{RN}, t_{RG}, t_{RT}, d_{IN}, d_{IG}, d_{IT}, d_{CN}, d_{CG}, d_{CT}, d_{KN}, d_{KG}, d_{KT}, d_{RN}, d_{RG}, d_{RT})$$

As explained above, this vector, as shown, is only an example displaying one term for each type of question (i.e., $t_{CN}$ stands for the response delay for a single control question asked to a single innocent control subject. In practice there may be many more terms (i.e., $t_{CN1}, t_{CN2}, t_{CN3}$, . . . standing for several questions to several control subjects.) The same holds true for the other types of questions and the other types of subjects. With this added information the neural net can improve on the classification of the test subject into a liar or a truth teller.

Figure 2:
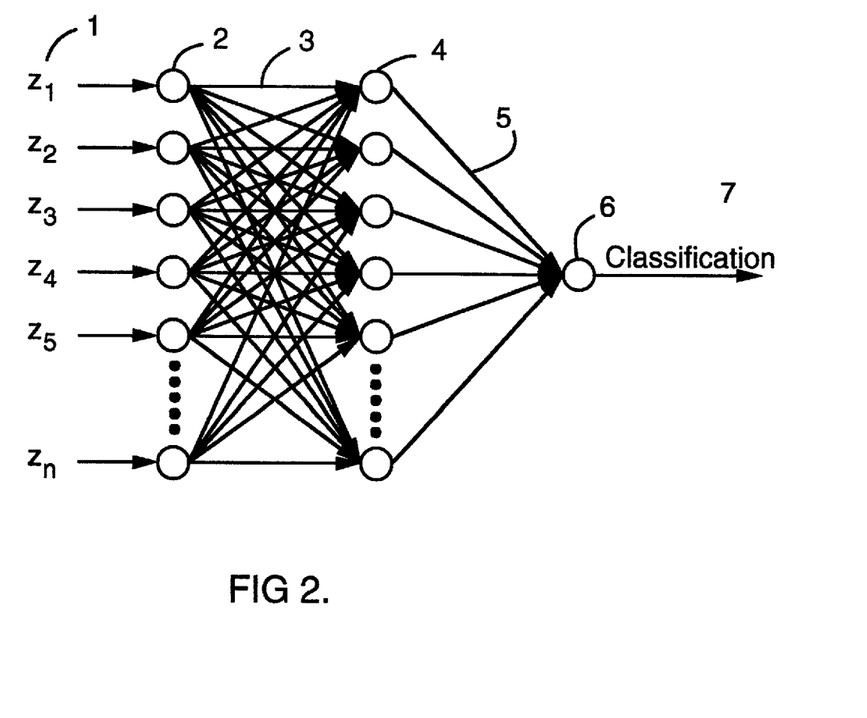
FIG. 2 shows how a neural net can be used to process data to generate a classification of the test subject.

As shown in FIG. 2, the input vector z 1 is fed to the first layer 2 of the neural net. The output from each node is then weighted by weights represented by the connections 3 and fed to the second layer 4. The outputs of the second layer are then weighted by the connection 5 and then fed to the output layer 6. This layer classifies the test subject into a truth teller or a liar 7.

One can train the neural net by means of a training algorithm such as backpropagation. More information on training algorithms can be found in *Artificial Neural Systems*, by Patrick K. Simpson.

Design of Question Set

To be effective, questions should maximize the difference between liars and truth tellers. Several methods are described below to amplify the effect of lying, to correct for various biases and errors introduced by the questioning process, and to counteract attempts at foiling lie detection. These include:

1) Surprise questions

2) Lying-on-Command

3) Use of Negatives and Double Negatives

Surprise Questions

The subject is confronted with an unforeseen question or with a question that incorporates knowledge that only the criminal knows about ("Guilty Knowledge"). The liar is forced to manufacture the lie on the spur of the moment and therefore delays his response. To be effective, questions should contain an element of surprise, and must be unlikely to have been rehearsed beforehand by the test subject. Therefore, the test must ideally be administered immediately without giving the subject the time to rehearse. (Countering rehearsal activity is discussed below.) Making use of Guilty Knowledge can in this context be a very effective way to elicit surprise.

Lying-on-Command

To augment the time delay caused by lying, the subject could be asked to intentionally lie to a question when a prearranged signal accompanies the question. This signal can be displayed on the monitor as a symbol, a letter or a shape, or can even be generated as a sound produced by the computer loudspeaker.

Since the liar has, in his mind, one more logical level than the truth teller, his task is more complex, and his response time is longer. The response time can be expressed as:

$$T_{resp} = T_{true} + T_{lie\,1}$$

When the subject is dishonest, the lie involves, for him, a double negative which is significantly harder to resolve than a simple lie. Under these conditions, the response of the dishonest person is significantly longer than that of an honest one, as represented in the equation below by the term $T_{lie2}$.

$$T_{resp} = T_{true} + T_{lie1} + T_{lie2}$$

Using control questions, we can solve for $T_{lie2}$ by subtracting the control response time from the incriminating response time as outline above.

Another approach called lying on command, involves extending the model already derived earlier using the product of L, E, Q, and S. Thus, for a test subject instructed to lie, the response time $T_{resp}$ can be modeled as:

$$T_{resp} = L_C L_T E Q_R S_T$$

where $L_C$=increase in response time due to lying on command

Measurements that include lying on command can be modeled by adding the additional state $L_C$ as shown below.

|  | Innocent Control Subject | Guilty Control Subject | Test Subject |
|---|---|---|---|
| Irrelevant Question | $L_C L Q_I S_N$ | $L_C Q_I S_G$ | $L_C Q_I S_T$ |
| Control Question | $L_C E Q_C S_N$ | $L_C E Q_C S_G$ | $L_C E Q_C S_T$ |
| Guilty Knowledge Question | $L_C Q_K S_N$ | $L_C E Q_K S_G$ | $L_C E Q_K S_T$ |
| Relevant Question | $L_C Q_R S_N$ | $L_C L_G E Q_R S_G$ | $L_C L_T E Q_R S_T$ |

The term $I_C$=log($L_C$) must then be appended to the state vector x which becomes:

$$x = (q_I, q_C, q_K, q_R, s_N, s_G, s_T, e, I_G, I_T, I_C)$$

The estimation techniques discussed earlier, including ratio methods, square root, Kalman filter and neural net, can easily be adapted to include this new state.

If the ratio method is used, then the terms carrying the factor $L_C$ just cancels out if the number of lying-on-demand questions in the numerator equals that in the denominator.

When a least square or Kalman filter technique is used, lying-on-command technique increases the dimensionality of the state vector by one element ($I_C$) but potentially doubles the number of types of questions in the measurement vector since each question may be asked in the normal way or with the lying-on-command feature enabled.

The effectiveness of lying-on-command in lie detection could be increased by giving rewards or punishments to the test subject. For example mild electric shocks associated with wrong answers to irrelevant and control questions with the lying-on-command feature enabled, could establish a motivation in the mind of the test subject for giving the correct answer to all questions. For example the question "Is the sky blue" with lying-on-command "on" should elicit the correct answer "No". A "Yes" answer triggers an electric shock. Thus a context in which truth is rewarded, is established in the mind of the test subject, who is then motivated to tell the truth or to delay a lie.

Clearly, while the electric shock method is convenient, there are many other choices for providing rewards or punishments to the test subject.

Negative and Double Negative Questioning

Adding logical inversions in questions creates additional logical levels in the mind of the subject being tested, that force him to delay his answer. When the question is in the negative form, the liar is at a disadvantage in comparison with the truth teller. While the truth teller must resolve a single negative, the liar must deal with a double negative which requires much longer time. If the test subject attempts to foil the test by rehearsing his answer, he may end up with a significantly faster answer than an honest person. In such cases, a variance analysis could detect rehearsal activity. An example of a question in the negative is:

Relevant question (Mrs. Johnson does have pies):
  Do you deny stealing a pie from Mrs. Johnson?
Control question (Mr. Anderson does not have pies):
  Do you deny stealing a pie from Mr. Anderson?

Different people have different abilities to resolve negative and double negative questioning. This uncertainty in response time can be taken out by the use of control questions applied to the test subject himself.

The approach taken earlier with lying-on-command can also be applied to the questions incorporating negatives and double negatives. An element can be added to the state vector x to model the effect of negatives and double negatives. The dimensionality of the measurement vector may double since each question can be asked either in the straightforward way or by adding a negative. The following are examples of questions with no negation, one negation, and two negations.

No Negation
  "Were you at the bank?"
  "Were you in your bed?"
One Negation
  "Were you out of the bank?" (implicit negation)
  "Were you out of your bed?" (implicit negation)
  "Do you deny being in the bank?" (explicit negation)
  "Do you deny being in your bed?" (explicit negation)
Two Negations
  "Do you deny being out of the bank?"
  "Do you deny being out of your bed?"
Three Negations
  "Do you deny not being out of the bank?"

"Do you deny not being out of your bed?"

Admittedly, the difficulty in answering such questions increases rapidly as the number of negatives increases, but the difficulty increases faster for the dishonest person than for the honest one. When the number of negatives in a question is about equal to, or is above two, the difficulty in providing an answer may become so high as to render the questions useless. Those questions then have "failed". They are simply be too difficult for the subject to answer. Variations from individual to individual in the ability to answer such questions, can be accounted for by means of the modeling techniques already discussed above, which include the ratio, least square, Kalman filter and neural nets methods.

Editing out of the response time database those responses that are wildly different from others can be used to eliminate failed questions. More refined editing methods are based on extensions of the estimation techniques already discussed. For example, Kalman filters compute residuals also called innovations. Very large residuals may indicate a failure of the question. Thus, editing out residuals too far away from the norm can eliminate data originating from failed questions.

Design of Question Presentation

The manner in which the questions are presented to the subject can be optimized to bring out attempts at deception and to reduce measurement biases. Three methods can be employed:

1) Randomized delayed display of key words
2) Randomization of questions order
3) Priming
4) Randomization of display delay

Randomized Delayed Display of Key Words

The reading, parsing and comprehension time can be significantly shortened by delaying the display of the key words that determine the truth or falsity of the sentence. This approach effectively reduces the signal to noise ratio by eliminating unnecessary time delays in the response. For example, the above questions could be rephrased as:

Control question (Mr Anderson does not have pies):
  Did you ever steal a pie from . . .
  (delay in computer display)
  Mr. Anderson? (Key word)
Relevant question (Mrs. Johnson does have pies):
  Did you ever steal a pie from . . .
  (delay in computer display)
  Mrs Johnson? (Key word)

Reading and comprehension of the preliminary part of the question does not contribute to the response time. Instead, the response time is measured as the time between the display of the key words and the binary response by the subject.

Randomization of Question Order

To eliminate interference in the response speed between adjacent questions, the questions can be arranged according to an order specified by the operator or by a computer-generated pseudo-random sequence.

Priming

Priming is the opposite of question order randomization. The question order is set manually to utilize context, to manipulate and exploit the frame of mind of the subject, and to trip him if he is a liar. This technique can be used in conjunction with guilty knowledge to elicit a stronger response.

Randomization of Display Delay

To enhance the effect of surprise, and to prevent a subject from anticipating when a question is about to be displayed, a random delay is set in the display of each question. Several methods can be used to implement this delay, such as:

1) Automatic Timer Initialization
2) Manual Timer Initialization

Automatic Timer Initialization

The questions appear on the screen one after the other. As soon as one question is answered, a timer is initiated with a pseudo-random count. At the completion of this pseudo-random count, the next question in line is displayed. The accuracy of the answer, and the time between the display of a question and the response of the subject is measured. The key entry event by the subject is used by the computer to initialize the pseudo-random count for the next question. The required sequence of events is as follows:

1) Subject or operator enters a start command
2) Pseudo-random clock is started
3) Pseudo-random clock times out—Question is displayed—Response time clock is started
4) Subject responds—response clock stops counting—response time is recorded—Question index is incremented—if there are any more questions, the program loops back to step 2. Otherwise the interrogation process stops.

Manual Timer Initialization

This process begins with the computer indicating that it is ready to display a question. When a key is hit, a timer is initialized with a fixed time of, for example, half a second to allow the subject to position himself appropriately to deliver his response. At the end of this time interval, the timer is restarted with a pseudo-random count to provide the element of surprise. At the end of the pseudo-random count, the question is displayed. The time and accuracy of the response are both measured. The process is then repeated for the next question. The required sequence of event is as follows:

1) The program waits for start/continuation command
2) Subject enters start/continuation command—Fixed time clock is started—Fixed time clock times out—Pseudo-random clock is started
3) Pseudo-random clock times out—Question is displayed—Response time clock is started
4) Subject responds—response clock stops counting—response time is recorded—Question index is incremented—if there are any more questions, the program loops back to step 1. Otherwise the interrogation process stops.

Selection of Concurrent Tasks Interfering With Lying

Lying may be associated with one area of the brain such as a brain hemisphere, or even more localized areas. Asking the subject to perform a task associated with the area mostly responsible for his lying activity may block or considerably slow down the lying process. This technique requires three steps:

1) Modeling the effect of interfering tasks on lying behavior
2) Identifying those tasks most effective in interfering with lying.
3) Requiring subjects to perform those tasks and collecting response time and data information.

Modeling the effect of interfering tasks on lying behavior

The increase in response time in a liar can be modeled as a sum of the normal response time plus a term caused by the execution of the task, as in $$T_{resp}=T_{true}+T_{lie}+T_{task}$$

Alternatively, we can extend the model derived above that uses factors L, E, Q, and S by adding a state A representing the assignment or task intended to interfere with lying. Thus the test subject response $T_{resp}$ becomes:

$$T_{resp}=AL_TEQ_RS_T$$

where

A=increase in response time due to tasking due to the assignment.

Identifying those tasks most effective in interfering with lying. Starting with a menu of tasks known to activate different brain areas, specific tasks can be identified that generate the greatest response delays when control and test subjects lie compared to when they tell the truth. Interfering tasks of interest include counting, adding, (simulated) driving, recognizing faces or objects, identifying colors.

Data for response times when such tasks are performed can be generated from innocent and guilty control subjects as well as from the test subject himself. For example, a guilty control subject could be asked to answer a relevant question, and therefore lie, while performing the task. Alternatively, a test subject could be asked to answer an irrelevant question with lying-on-command enabled, while performing the task.

Information of interest to the selection process includes not only the time response of the subject to the questions, but also the execution time delay of the subject in performing the task. A possible implementation would thus employ as input to the estimation process, the sum of the answer response time plus the task execution time delay.

These sums can be expressed, for example, as:

$$T_{resp+task/Lying-On-Command}=T_{resp}+T_{task/Lying-On-Command}$$

and $$T_{resp+task/truth}=T_{resp}+T_{task/truth}$$

An index R can be calculated from response time measurements to compare two tasks in their ability to interfere with lying activity. R can be expressed as:

$$R=\frac{T_{resp+task1/Lying-On-Command}}{T_{resp+task2/Lying-On-Command}} \cdot \frac{T_{resp+task2/truth}}{T_{resp+task1/truth}}$$

Alternatively, measurements taken when tasks are performed could be modeled as shown below:

|  | Innocent Control Subject | Guilty Control Subject | Test Subject |
| --- | --- | --- | --- |
| Irrelevant Question | $AQ_IS_N$ | $AQ_IS_G$ | $AQ_IS_T$ |
| Control Question | $AEQ_CS_N$ | $AEQ_CS_G$ | $AEQ_CS_T$ |
| Guilty Knowledge Question | $AQ_KS_N$ | $AEQ_KS_G$ | $AEQ_KS_T$ |
| Relevant Question | $AQ_RS_N$ | $AL_GEQ_RS_G$ | $AL_TEQ_RS_T$ |

As explained above, a state vector x and a measurement vector y can be created as a basis for employing an estimation technique such as least square, Kalman filters and neural nets. The state vector would then include the term a=log(A) to represent the effect of the task of lying.

Application of concurrent task to interrogation process.

Once the task that maximizes response delays is identified, then it can be assigned to the test subject during the interrogation procedure. As was done earlier, an index ratio R can be calculated from measurements, or an estimation technique such as least square, Kalman filter or neural nets could be employed to solve for the state vector x and the element $I_T$ from which the index $L_T$ can be calculated as follows:

$$L_T=\text{antilog}(I_T)$$

More elaborate algorithms can be used to combine information involving control subjects and test subjects and thus provide a more secure lie detection process immune to the countermeasures of a liar.

Countering Rehearsal

Rehearsing the answer to a question can be detected because it changes the response profile of the subject and may result in abnormal shorter response time for test questions. Answers to control and irrelevant questions which are too slow, may indicate intentional delays. A profile for response times of the test subject and of the control subjects for relevant, control and irrelevant questions can provide a basis for classifying the test subject as a liar or a truth-teller. Statistical techniques can be used to compare the response time distribution of the test subject with the distribution of a control subject and thus ferret out the deceiving liar. Backpropagation is an effective algorithm for teaching a neural nets to classify liars from truth-tellers when experimental information is readily available but a model is unproven or nonexistent.

Remote Operation

Because of the simplicity of the measured response time data, it is possible to readily operate this lie detection system remotely over a radio or telecommunication link.

Questions could be presented in two possible formats: video and audio. Responses could be entered either with a manual data entry device such as a keyboard, a mouse or a joystick, or with a voice-activated/voice-recognition device.

Integration With Other Lie Detection Techniques

This invention could be used by itself or in conjunction with a conventional polygraph. By itself, it has the advantage of requiring only a computer with the usual associated hardware (real time clock, monitor and keyboard). When used in conjunction with a polygraph, it can provide an additional degree of certainty to the lie detection process.

Description of Hardware

The device can simply be implemented by means of a computer equipped with standard hardware features such as a monitor, a hard disk, a keyboard and a real-time-clock for measuring the response time and for generating pseudo-random time intervals. It may also utilize a joystick to facilitate response time measurement, a modem to enable remote testing, a sound system to permit audio interrogation and voice response, and a printer to allow the production of hard copy reports.

Description of Software

The software comprises the following modules:
1) Questionnaire composition database program
2) Database presentation and interrogation software
3) Response measurement software
4) Response analysis software Questionnaire composition database program A database of questions can be implemented on a computer using a custom-made data entry program, a conventional database program or more simply a word processing program.

The database mechanism includes a means to allow the operator to enter a list of questions and label each question according to its type or attribute (irrelevant/control/guilty knowledge/relevant/lying-on-command/negative), its order in the display sequence, the identity and location of its key words, the amount and type of delay to be used, and the processing to be applied to the collected reaction time data.

Several methods can be used to achieve this labeling. For example, if a conventional word processor program is used, a command sequence enclosed in brackets can be appended to each question by the operator composing the questionnaire. The software decodes and executes this command sequence. The labels would be stripped off when the questions are presented to the subjects during testing. For example labels indicating the sequence and the nature of the questions could be written by the operator as follows:

Control question (Mr. Anderson does not have pies)
[10, Control, Lie-On-Command On] Did you ever steal a pie from Mr. Anderson?

Test question (Mrs. Johnson does have pies)
[5, Relevant, Lie-On-Command Off] Did you ever steal a pie from Mrs Johnson?

The database mechanism should also allow the measurement to be labeled according to which subject (innocent control, guilty control, or test) provided the answer. The interrogation data base should include the response time as well as nature of the answers (e.g., "yes","no"). Information regarding the nature of the subject could be entered at the beginning of the test session for a particular subject by selecting one item from the menu below:

1) Innocent Control Subject
2) Guilty Control Subject
3) Test Subject

Window mechanisms and graphical user interfaces can greatly simplify the data entry mechanisms for questions, subjects and corresponding control codes.

Database presentation and interrogation software

This module controls the delivery of questions to the test subject and allows the operator to display the questions either according to a prearranged manner, or according to some pseudo-random ordering. In addition, a pseudo-random delay can be applied to each question or to key words comprising a question, as already described above, by means of an automatic timer initialization process or a manual timer initialization process.

The software also include the lying-on-command feature by allowing the operator to present on a controlled basis (i.e., pseudo-random, manual or other scheme) a flag or signal ordering the subject to lie, that would appear approximately at the same time a question is displayed.

This module also allows the operator to control the presentation of an task interfering with lying, to, and its execution by, the subject.

Response measurement software

This module allows manual or vocal entries by the test subject, measures the time between the display of the question to the subject and the response to the question, and builds a database of response times, response data, and concurrent tasks performance data.

Response analysis software

This module allows the operator to perform a statistical analysis on response delays, response data and concurrent task performance data.

Noise in response time measurements and in answer accuracy can be reduced by performing several measurements for the same questions. This set of measurements can be edited on the basis of the accuracy and consistency of the answers. For example, response times that are too far away from the mean could be deleted to provide a more consistent data set. The remaining measurements can then be employed to compute a mean and a variance which can be used in the liar/truth teller classification task.

More generally, statistical analysis, neural net technology or similar types of mathematical methods can be used to classify test subjects as honest or dishonest as well as improve the questionnaire. Specifically these methods can be applied to identify:

how liars differ in their response from truth tellers which type of questions are the best discriminators which signal amplification technique is the most effective such as lying-on-command, double negatives, concurrent tasking which noise reduction technique is the most effective such as randomization and delay of key words While the above description contains many specificities, the reader should not construe these as limitations on the scope of the invention, but merely as exemplifications of preferred embodiments thereof. Those skilled in the art will envision many other possible variations within its scope. Accordingly, the reader is requested to determine the scope of the invention by the appended claims and their legal equivalents, and not by the examples which have been given.

I claim:

1. A lie detection device that relies on the voluntary motor reaction time of a subject to a set of questions, said device comprising a computer, said computer itself comprising:

a question data entry means for a human operator to enter said set of questions into memory of said computer, said set of questions henceforth called a questionnaire, a question data presenting means which is operatively connected to said computer memory for presenting said questionnaire to said subject, presenting process of said questionnaire henceforth called interrogation, said presenting means comprising a means for retrieving one question at a time from said stored questionnaire and for displaying said question, a response data entry means for said subject to enter responses to said question into memory of said computer, said responses being based on voluntary physical motor action by said subject and said responses henceforth called response data, a real time clock operationally connected to said question data presenting means and also operationally connected to said response data entry means, for measuring the time elapsed between the presentation of said question by presenting means, and the detection of said response by response data entry means, said time henceforth called response time, said response time being stored in memory of said computer, said ensemble of said questions, said response data, and said response time being defined as interrogation database, a memory controller which uses the information in said interrogation database to calculate a classification index that assigns to said subject, degrees of membership to a liar class or a truth-teller class.

2. A device as in claim 1 wherein said response data entry means is adapted to be manually operated by said subject.

3. A device as in claim 1 wherein said response data entry means comprises a voice recognition means, and is adapted to be orally operated by said subject.

4. A device as in claim 1 wherein said means for entering responses is adapted to receive a binary response.

5. A device as in claim 1 wherein said means for entering responses is adapted to receive a unary response.

6. A device as in claim 1 wherein said question data presenting means is adapted to allow said operator to manually set the order of said questions.

7. A device as in claim 1 wherein said question data presenting means is adapted to present each question to said subjects after a delay of random length.

8. A device as in claim 1 wherein said question data presenting means is a video device.

9. A device as in claim 1 wherein said question data presenting means is an audio device.

10. A device as in claim 1 wherein said subjects are classified into at least two classes comprising innocent control subjects and test subjects, and said memory controller includes means for utilizing said response data from said innocent control subjects and said response data from said test subjects, whereby generating a more reliable said classification index for said test subjects.

11. A device as in claim 1 wherein said subjects are classified into at least two classes comprising guilty control subjects and test subjects, and said memory controller includes means for utilizing said response data from said guilty control subjects and said response data from said test subjects, whereby generating a more reliable said classification index for said test subjects.

12. A device as in claim 1 wherein questions are classified into at least two classes, one of these classes being irrelevant questions, and said memory controller includes means for utilizing said response data from at least said irrelevant questions, whereby generating a more reliable said classification index for said subjects.

13. A device as in claim 1 wherein questions are classified into at least two classes, one of these classes being control questions, and said memory controller includes means for utilizing said response data from at least said control questions, whereby generating a more reliable said classification index for said subjects.

14. A device as in claim 1 wherein questions are classified into at least two classes, one of these classes being guilty knowledge questions, and said memory controller includes means for utilizing said response data from at least said guilty knowledge questions, whereby generating a more reliable said classification index for said subjects.

15. A device as in claim 1 wherein questions are classified into at least two classes, one of these classes being surprise questions, and said memory controller includes means for utilizing said response data from at least said surprise questions, whereby generating a more reliable said classification index for said subjects.

16. A device as in claim 1 wherein said question data entry means is adapted to allow said operator to enter lying-on-command flags, assign to them a binary possible value "ON" or "OFF," and associate each said lying-on-command flag to any said question in said questionnaire, and said question data presenting means is adapted to use said lying-on-command flag to signal said subject to lie when the value of said lying-on-command flag is "ON," when said question associated with said lying-on-command flag is presented to said subject.

17. A device as in claim 1 wherein said question data entry means is adapted to allow said operator to enter the expected true response of said subject to said questions in said questionnaire, and said question data including means for presenting a reward to said subject when said response of said subject to said questions agrees with said expected response to said questions.

18. A device as in claim 1 wherein said question data entry means is adapted to allow said operator to enter the expected true response of said subject to said questions in said questionnaire, and said question data presenting means including means for presenting a punishment to said subject when said response of said subject to said questions does not agrees with said expected response to said questions.

19. A device as in claim 1 wherein said question data entry means is adapted to allow said operator to enter said questions with at least one negative.

20. A device as in claim 1 wherein said question data entry means said operator to mark any words embedded in any of said questions as key words, and said question data presenting means including means for delaying the presentation of any said key word with respect to the presentation of any said question in which said keyword is embedded.

21. A device as in claim 1 wherein said question data presenting means including means for randomizing the order of said questions.

22. A device as in claim 1 wherein said memory controller comprises a means for collecting the ensemble of said questions and said responses into an interrogation database stored in said computer memory.

23. A device as in claim 1 wherein said question data entry means is adapted to allow said operator to mark any said question with a concurrent task name, and said question data presenting means including means for presenting said concurrent task name to said subject at approximately the same time said question associated with said concurrent task is presented, with the understanding that said subject is supposed to execute said concurrent task while responding to said questions.

24. A device as in claim 23 wherein said subjects uses said question data response means to perform said concurrent task, and said memory controller includes means for collecting performance data on said concurrent task from said question data response means, and for storing said data into said interrogation database.

25. A device as in claim 1, further comprising communication hardware and software operationally connected to said computer, to allow said subject to be interrogated at a remote location.

26. A device as in claim 1 wherein said memory controller is adapted to edit out of said interrogation database, said response times that differ more than a set amount from the norm.

27. A device as in claim 1 wherein said memory controller is adapted to use at least one parameter of a set of parameters describing the mental and physical states of said subject, and the reading and comprehension difficulty of said questions, said set of parameters including the increase in said response time, L, due to lying, the time delay factor, E, in said response time caused by the emotional content of said question, the variations, S, in response time, caused by the mental and physical state of said subject, the increase, Q, in said response time required to parse and comprehend said question, to generate said classification index of said subject into a liar or a truth-teller.

28. A device as in claim 1 wherein said memory controller is adapted to use Least Square calculation to estimate said classification index of said subject into a liar or a truth-teller.

29. A device as in claim 1 wherein said memory controller is adapted to use Kalman Filter calculation to estimate said classification index of said subject into a liar or a truth-teller.

30. A device as in claim 1 wherein said memory controller is adapted to use a ratio calculation to estimate said classification index of said subject into a liar or a truth-teller.

31. A device as in claim 1 wherein said memory controller is adapted to use a neural net calculation to estimate said classification index of said subject into a liar or a truth-teller.

* * * * *